(12) United States Patent
Huffstodt et al.

(10) Patent No.: US 9,395,373 B2
(45) Date of Patent: *Jul. 19, 2016

(54) HYBRID STRIP

(71) Applicant: Polymer Technology Systems, Inc., Indianapolis, IN (US)

(72) Inventors: Robert Huffstodt, Indianapolis, IN (US); James J. Sutor, Greenwood, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 478 days.

This patent is subject to a terminal disclaimer.

(21) Appl. No.: 13/843,116

(22) Filed: Mar. 15, 2013

(65) Prior Publication Data

US 2013/0217054 A1 Aug. 22, 2013

Related U.S. Application Data

(63) Continuation-in-part of application No. 12/997,781, filed as application No. PCT/US2009/047100 on Jun. 11, 2009, now Pat. No. 8,460,539.

(60) Provisional application No. 61/061,506, filed on Jun. 13, 2008.

(51) Int. Cl.
*G01N 27/327* (2006.01)
*G01N 33/66* (2006.01)
(Continued)

(52) U.S. Cl.
CPC ............... *G01N 33/66* (2013.01); *G01N 21/77* (2013.01); *G01N 27/3272* (2013.01); *G01N 33/525* (2013.01); *G01N 33/558* (2013.01); *G01N 33/92* (2013.01)

(58) Field of Classification Search
CPC ....... G01N 27/327–27/3272; G01N 2021/035; G01N 2021/752; G01N 2021/77
See application file for complete search history.

(56) References Cited

U.S. PATENT DOCUMENTS

| | | |
|---|---|---|
| 4,225,410 A | 9/1980 | Pace |
| 5,213,964 A | 5/1993 | Jones |

(Continued)

FOREIGN PATENT DOCUMENTS

| | | |
|---|---|---|
| EP | 0034049 A1 | 8/1981 |
| EP | 1318397 A1 | 6/2003 |
| EP | 1471354 A2 | 10/2004 |

OTHER PUBLICATIONS

Office Action and Search Report in co-pending European Patent Application No. 14768248.8 dated Apr. 1, 2016 (8 pages).

*Primary Examiner* — Alexander Noguerola
(74) *Attorney, Agent, or Firm* — Haynes and Boone LLP; Robert P. Ziemian

(57) ABSTRACT

A method of determining concentrations of a plurality of analytes from a single blood sample placed in a single opening. A portion of the single blood sample is absorbed by a test matrix that includes a plurality of layers and a chromogenic agent. A colored response is generated by the test matrix. The colored response is proportional to the concentration of a first analyte. A portion of the single blood sample is drawn into a capillary tube and placed in contact with an electrode and a counter-electrode. An electrical property of the single blood sample is analyzed through the electrode and counter-electrode. The electrical property is proportional to the concentration of a second analyte in the single blood sample.

20 Claims, 10 Drawing Sheets

(51) Int. Cl.
*G01N 21/77* (2006.01)
*G01N 33/52* (2006.01)
*G01N 33/558* (2006.01)
*G01N 33/92* (2006.01)

(56) References Cited

U.S. PATENT DOCUMENTS

| | | |
|---|---|---|
| 5,316,916 A | 5/1994 | Jones |
| 5,426,030 A | 6/1995 | Rittersdorf et al. |
| 5,451,370 A | 9/1995 | Jones |
| 5,580,743 A | 12/1996 | Rittersdorf et al. |
| 5,597,532 A | 1/1997 | Connolly |
| 5,786,164 A | 7/1998 | Rittersdorf et al. |
| 6,171,849 B1 | 1/2001 | Rittersdorf et al. |
| 6,214,570 B1 | 4/2001 | Rittersdorf et al. |
| 6,309,526 B1 | 10/2001 | Fujiwara et al. |
| 6,881,578 B2 * | 4/2005 | Otake .................. 436/44 |
| 6,884,592 B2 * | 4/2005 | Matzinger et al. ........ 435/7.1 |
| 8,460,539 B2 * | 6/2013 | Huffstodt et al. ........ 205/792 |
| 2003/0068666 A1 | 4/2003 | Zweig |
| 2004/0126830 A1 | 7/2004 | Shull et al. |
| 2005/0003523 A1 | 1/2005 | Anaokar et al. |
| 2011/0155590 A1 | 6/2011 | Huffstodt |

* cited by examiner

*FIG. 10*
*FIG. 11*
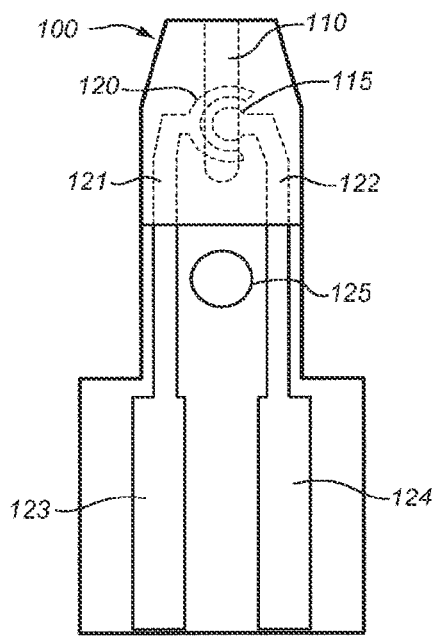
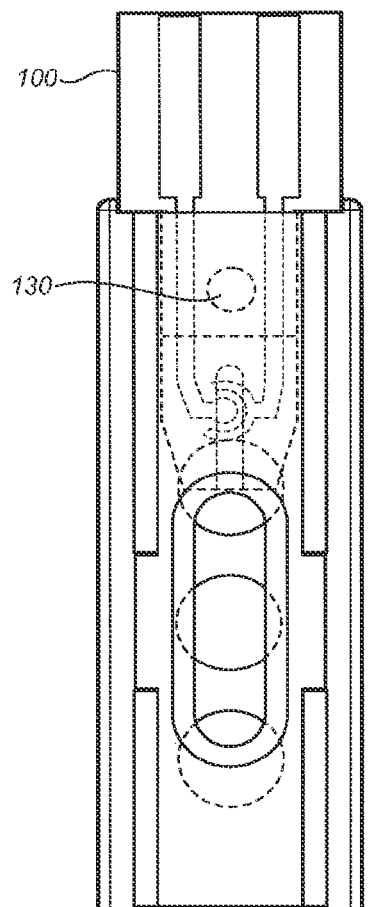
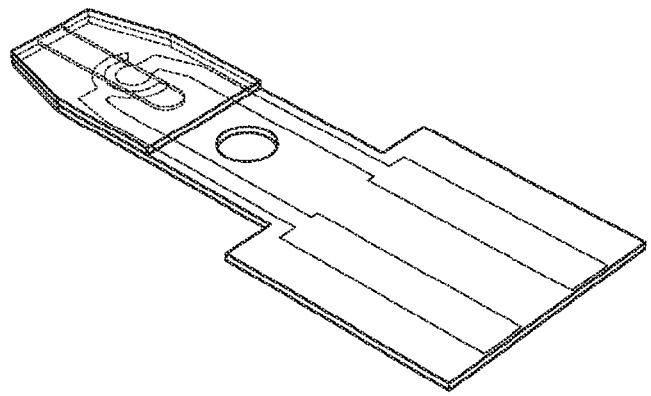
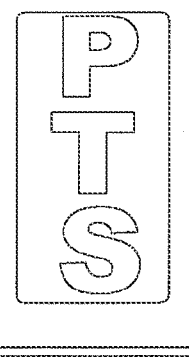

HYBRID STRIP

CROSS-REFERENCE TO RELATED APPLICATIONS

This Application is a continuation-in-part of U.S. patent application Ser. No. 12/997,781 filed Mar. 11, 2011, which application claims the benefit of: U.S. Provisional Application No. 61/061,506 filed on Jun. 13, 2008, which applications are hereby incorporated by reference to the same extent as though fully disclosed herein.

BACKGROUND OF THE INVENTION

The level of certain analytes in blood and other body fluids is often used to diagnose disease, determine disease risk factors, monitor the course of a therapy, or determine the presence of illicit drugs. In recent years, analytes carried in blood have been evaluated to determine various cholesterol and triglyceride levels as a significant indicator of risk of coronary heart disease. In managing heart disease, physicians commonly order what is referred to in the art as a "full lipid panel" for patients to determine the concentration of total cholesterol, high density lipoprotein cholesterol (HDL), low density lipoprotein cholesterol (LDL), and triglycerides. Glucose and ketone dry hybrid test strips are used for managing diabetes. Ketone hybrid test strips also are useful in managing weight loss. Hybrid test strips for determining creatinine concentration in the blood or other bodily fluids are used for diagnosing and treating impaired kidney function and a variety of other metabolic disorders and diseases.

While clinical tests have been used and still are being used to determine the concentration of the above-mentioned analytes, more and more physicians and consumers are relying on dry hybrid test strips for economical and easier measurement, particularly when testing at shorter intervals, such as days or weeks, is important or when rapid results are critical. Furthermore, for such tests to be practical for consumers and physicians, the devices used for testing must be small and portable. For certain users, diabetics testing for glucose levels for example, portability is key since glucose levels must be frequently tested to maintain proper insulin levels. As a result of this need, numerous small and portable devices have been developed to test for analytes.

The mechanisms used in determining the levels of analytes in the blood fall into a number of categories, including but not limited to: photometric, electrochemical (ampherometric and coulmetric), and potentiometric. Photometric blood testing typically involves reacting a blood sample with a reagent, shining a light on the reacted sample, and measuring the light reflected. Electrochemical blood testing involves reacting the blood with a reagent, subsequently applying an excitation voltage to the reacted sample, and measuring the effect of the excitation voltage. Potentiometric testing involves measuring the potential (or voltage) using analyte specific electrodes.

Presently available devices perform tests according to one of the above-mentioned mechanisms. Since the mechanisms require significantly different systems, to keep devices small, an omnibus device has not been created. Furthermore, many users only need to test for a single analyte and, therefore, a system performing tests according to a single mechanism would meet their needs.

Diabetes and heart disease are "silent killers" that affect more than 200 million Americans. Since 1900, heart disease has been the leading cause of death in the United States, costing the health care system more than $326.6 billion annually. Risk of heart disease or stroke is 2 to 4 times greater for people with diabetes than for the average person. Of people receiving diagnoses of type 2 diabetes, 50% are not aware of their risk until after their first heart attack or stroke. For most of the patients with type 2 diabetes, an average of 7 to 10 years elapses from the time that heart disease develops to its diagnosis.

BRIEF SUMMARY OF THE INVENTION

Since many individuals who suffer from diabetes also are at risk for heart disease, such individuals or their physicians may desire that they regularly test not only for glucose levels related to their diabetic condition, but also for various cholesterol and triglyceride levels as a significant indicator of risk of coronary heart disease. Presently, a user is unable to run both an electrochemical test yielding glucose levels and a photometric test yielding various cholesterol and triglyceride levels with a single device and a single strip. Not only would a user need to have two separate devices, the user would need to take two separate blood samples. The time required to perform two tests and the need to take two blood samples discourages many individuals from routinely performing such tests as needed or directed by their doctor.

Furthermore, some individuals suffer from conditions that make certain test mechanisms for analytes ineffective. Examples of some of these conditions include, but are not limited to: sickle-cell disease, end-stage renal disease, or other conditions that alter hemoglobin/hematocrit (dehydration, anemia). Individuals with such conditions must use technologies that minimize the interference from hematocrit levels. This typically requires electrochemical testing techniques. At the same time, electrochemical testing techniques do not allow the individual to test for certain analytes; they may only efficiently be tested by using photometric techniques.

A solution to the above problems is offered by providing a hybrid strip and device for utilizing the hybrid strip that allows for the testing of multiple analytes by a variety of methods. These methods include photometric testing methods and electrochemical testing techniques, including coulmetric, potentiometric, and amphermetric techniques.

In one embodiment of a method of determining concentrations of a plurality of analytes from a single blood sample, placed in a single opening, a hybrid test strip includes electrochemical and photochemical testing mechanisms to determine the concentration of various analytes. A portion of the single blood sample is absorbed by a test matrix that includes a plurality of layers and a chromogenic agent. A colored response is generated by the test matrix. The colored response is proportional to the concentration of a first analyte. A portion of the single blood sample is drawn into a capillary tube and placed in contact with an electrode and a counter-electrode. An electrical property of the single blood sample is analyzed through the electrode and counter-electrode. The electrical property is proportional to the concentration of a second analyte in the single blood sample.

In one embodiment of a method of determining concentrations of a plurality of analytes from a single blood sample using a hybrid test strip, placed in a single opening, the single blood sample is contacted with the top surface of an elongated disbursement layer. The sample is spread substantially throughout the entire length of the disbursement layer. The single blood sample is contacted with the end of a capillary tube, such that a portion of the single blood sample is drawn into the capillary tube. The blood sample is delivered from the disbursement layer to a first stack, a second stack, and a third stack, each of the first, second, and third stacks positioned adjacent to and in constant contact with the disbursement layer. The sample is moved downward through the stacks including through the blank layer in a direction substantially normal to the plane defined by the stacks. A colored response is produced at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample. A portion of the single blood sample drawn into the capillary tube is delivered to an electrode and a counter-electrode. An electrical property of the single blood sample is measured using the electrode and counter-electrode. The electrical property is proportional to the concentration of a fourth analyte in the blood sample. In one alternative, the sample chamber further includes a loosely woven material that assists in the flow of the sample to the electrodes. In this alternative, the sample chamber may not utilize a capillary effect. In another alternative, the sample chamber may also not utilize the capillary effect but instead the permissively of the spreading layer is sufficient to spread the sample into the sample chamber.

In an embodiment of an apparatus for measuring concentration of multiple analytes in a whole blood sample, a hybrid test strip is used. The apparatus includes a test matrix having an elongated porous disbursement layer, a blood separation layer adjacent to the bottom surface of the disbursement layer, and at least two vertically aligned stacks spaced apart and adjacent to the bottom surface of the blood separation layer. A first one of the vertically aligned stacks includes multiple layers, the multiple layers including a reagent and a chromagen. The apparatus further includes an electrochemical testing member that includes a capillary tube having a first end and a second end, an electrode, and a counter-electrode. The electrode and counter-electrode are oriented in electrical communication with each other when a blood sample is present. A hybrid test strip holder having top and bottom portions sandwiches the test matrix between the top and bottom portion. The top and bottom portions hold the electrochemical testing member. The top portion of the hybrid test strip holder has a sample application window exposing a top surface of the disbursement layer and the first end of the capillary tube. The bottom portion of the hybrid test strip holder has at least one test reading window through which bottom surfaces of the first and second stacks can be read.

An embodiment of a method of using a hybrid test strip for determining concentrations of a plurality of analytes from a single blood sample, placed in a single opening, includes separating a top portion of a hybrid test strip holder from the bottom portion of a hybrid test strip holder. An electrode chemical testing member is placed on the bottom portion of the hybrid test strip holder such that a hole in the electrode chemical testing member is on a rod of the bottom portion. The top portion of the hybrid test strip holder and the bottom portion of the hybrid test strip holder are connected such that the electrochemical testing member is sandwiched between. The hybrid test strip holder houses a test matrix that includes an elongated porous disbursement layer, a blood separation layer adjacent to the bottom surface of the disbursement layer, and at least two vertically aligned stacks spaced apart and adjacent to the bottom surface of the blood separation layer, wherein a first one of the vertically aligned stacks includes multiple layers, the multiple layers including a reagent and a chromagen.

One embodiment of a method of determining concentrations of a plurality of analytes from a single blood sample, placed in a single opening, includes placing the single blood sample in an opening; absorbing the blood sample with a test matrix that includes a plurality of layers and a chromogenic agent; generating a colored response with the test matrix, wherein the colored response is proportional to the concentration of a first analyte; drawing a portion of the single blood sample into a capillary tube; contacting the portion of the single blood sample with an electrode and a counter-electrode; and measuring an electrical property of the single blood sample though the electrode and counter-electrode, wherein the electrical property is proportional to the concentration of a second analyte in the single blood sample. One feature of the method is that the drawing may be accomplished by a capillary effect of the capillary tube.

In another embodiment, a method of determining concentrations of a plurality of analytes from a single blood sample, placed in a single opening, includes: contacting the single blood sample with the top surface of an elongated disbursement layer and spreading the sample substantially throughout the entire length of the disbursement layer; contacting the single blood sample with the end of a capillary tube, such that a portion of the single blood sample is drawn into the capillary tube; delivering the blood sample from the disbursement layer to a first stack, a second stack, and a third stack, each of the first, second, and third stacks positioned adjacent to and in constant contact with the disbursement layer, and moving the sample downward through the stacks in a direction substantially normal to the plane defined by the stacks; producing a colored response at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample; delivering the portion of the single blood sample drawn into the capillary tube to an electrode and a counter-electrode; and measuring an electrical property of the single blood sample using the electrode and counter-electrode, wherein the electrical property is proportional to the concentration of a fourth analyte in the blood sample.

One feature of the method is that at least one of the stacks includes a blank layer, the blank layer being a different layer than the disbursement layer. The blank layer primarily functions to maintain all stacks at substantially the same thickness. Another feature may include that the first, second, and third analytes are Total Cholesterol, HDL Cholesterol, and Triglycerides respectively. Another feature may include that the fourth analyte is glucose. Another feature may include a selectively permeable membrane introduced between the electrode and counter-electrode in order to lessen interferents. Another feature may include a selective electrocatalyst introduced in order to lessen interferents.

An embodiment of an apparatus for measuring a concentration of multiple analytes in a whole blood sample includes a test matrix, an electrochemical testing member, and a hybrid test strip holder having top and bottom portions sandwiching the test matrix therebetween and the top and bottom portions holding the electrochemical testing member, the top portion of the hybrid test strip holder having a sample application window exposing a top surface of a disbursement layer and a first end of a capillary tube, and a bottom portion of the hybrid test strip holder having at least one test reading window through which bottom surfaces of the first and second stacks can be read. The test matrix includes an elongated porous disbursement layer; a blood separation layer adjacent to the bottom surface of the disbursement layer; and at least two vertically aligned stacks spaced apart and adjacent to the bottom surface of the blood separation layer wherein a first one of the vertically aligned stacks includes multiple layers, the multiple layers including a reagent and a chromagen. The electrochemical testing member includes a capillary tube having a first end and a second end; an electrode; and a counter-electrode, wherein the electrode and counter-electrode are oriented in electrical communication with each other when a blood sample is present.

A feature of the apparatus includes that the sample application window is positioned within a periphery defined by the stacks. Another feature includes that the bottom surfaces of the stacks are substantially coplanar. Another feature includes that the blood separation layer comprises a glass fiber matrix. Another feature includes that the electrochemical test panel includes enzymatic reactants overlaying the electrode and counter-electrode. Another feature includes that a selectively permeable membrane is introduced between the electrode and counter-electrode in order to lessen interferents. Another feature includes that a selective electrocatalyst is introduced in order to lessen interferents. Another feature includes that the electrochemical testing member is interchangeable.

In an embodiment of a method of customizing a hybrid test strip for determining concentrations of a plurality of analytes from a single blood sample, placed in a single opening, the method includes separating a top portion of a hybrid test strip holder from the bottom portion of a hybrid test strip holder, the bottom portion of the hybrid test strip holder having a rod; placing an electrode chemical testing member on the bottom portion of the hybrid test strip holder such that a hole in the electrode chemical testing member is on the rod of the bottom portion; and connecting the top portion of the hybrid test strip holder and the bottom portion of the hybrid test strip holder such that the electrochemical testing member is sandwiched between. In this embodiment, the hybrid test strip holder houses a test matrix including an elongated porous disbursement layer, a blood separation layer adjacent to the bottom surface of the disbursement layer, and at least two vertically aligned stacks spaced apart and adjacent to the bottom surface of the blood separation layer. A first one of the vertically aligned stacks includes multiple layers, the multiple layers including a reagent and a chromagen. A feature of an embodiment includes the capability to tailor the hybrid strip to test for a variety of analytes according to the optimal testing methodology.

In another embodiment as system for sample retention using a test strip having a body. Within the body is a spreader layer configured to evenly spread the fluid sample received through the port. Multiple sample retention areas and test areas may be included in the body of the test strip.

In another embodiment, a method of determining concentrations of a plurality of analytes from a single blood sample, placed in a single opening includes placing the single blood sample in an opening. The method further includes absorbing the blood sample with a test matrix that includes a plurality of layers and a chromogenic agent, the test matrix including a disbursement layer. The method further includes generating a colored response with the test matrix and the colored response is proportional to a concentration of a first analyte. The method further includes drawing a portion of the single blood sample to a sample area by laterally spreading through the disbursement layer. The method further includes contacting the portion of the single blood sample with an electrode and a counter-electrode in the sample area. The method further includes measuring an electrical property of the single blood sample though the electrode and counter-electrode and the electrical property is proportional to a concentration of a second analyte in the single blood sample.

In another embodiment, a method of determining concentrations of a plurality of analytes from a single blood sample includes contacting the single blood sample with a top surface of an elongated disbursement layer and spreading the single blood sample substantially throughout an entire length of the disbursement layer. The method further includes contacting the single blood sample with a sample area such that a portion of the single blood sample is drawn to the sample area by passing through the disbursement layer. The method further includes delivering the single blood sample from the disbursement layer to a first stack, a second stack, and a third stack, each of the first, second, and third stacks positioned adjacent to and in constant contact with the disbursement layer. The method further includes moving the sample downward through the stacks in a direction substantially normal to the plane defined by the stacks. The method includes producing a colored response at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample. The method further includes delivering the portion of the single blood sample drawn into the sample area to an electrode and a counter-electrode. The method further includes measuring an electrical property of the single blood sample using the electrode and counter-electrode and the electrical property is proportional to the concentration of a fourth analyte in the blood sample. Optionally, the first, second, and third analytes are Total Cholesterol, HDL Cholesterol, and Triglycerides, respectively. Optionally, the fourth analyte is glucose.

In another embodiment, a method of determining concentrations of a plurality of analytes from a single blood sample includes contacting the single blood sample from a lance with a top surface of an elongated disbursement layer of a test strip and spreading the single blood sample substantially throughout an entire length of the disbursement layer. The method further includes contacting the single blood sample with a sample area of an electrochemical portion of the test strip, and a residual amount of the single blood sample remaining previous contacting is used. The method further includes delivering the single blood sample from the disbursement layer to a first stack, a second stack, and a third stack, each of the first, second, and third stacks positioned adjacent to and in constant contact with the disbursement layer. The method further includes moving the sample downward through the stacks in a direction substantially normal to the plane defined by the stacks. The method further includes producing a colored response at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample. The method further includes measuring an electrical property of the single blood sample using the electrode and counter-electrode in the electrochemical portion, and the electrical property is proportional to the concentration of a fourth analyte in the blood sample. Optionally, the first, second, and third analytes are Total Cholesterol, HDL Cholesterol, and Triglycerides, respectively and the fourth analyte is glucose.

In another embodiment, an apparatus for measuring concentration of multiple analytes in a whole blood sample includes a test matrix having an elongated porous disbursement layer; a blood separation layer adjacent to the bottom surface of the disbursement layer; and at least two vertically aligned stacks spaced apart and adjacent to the bottom surface of the blood separation layer and a first one of the vertically aligned stacks includes multiple layers, the multiple layers including a reagent and a chromagen. The apparatus further includes an electrochemical testing member includes a sample area; an electrode; and a counter-electrode and the electrode and counter-electrode are oriented in electrical communication with each other when a blood sample is present, and the electrode and the counter-electrode located in the sample area. The apparatus further includes a hybrid test strip holder having a top portion and a bottom portion sandwiching the test matrix there between; the top and bottom portions holding the electrochemical testing member; the top portion of the hybrid test strip holder having a sample application window exposing a top surface of the disbursement layer and a portion of the disbursement layer in contact with the sample area, such that blood from the disbursement layer may reach the sample area when a sample is present; and the bottom portion of the hybrid test strip holder having at least one test reading window through which bottom surfaces of the first and second stacks can be read. Optionally, the sample application window is positioned within a periphery defined by the stacks. In one alternative, the bottom surfaces of the stacks are substantially coplanar. In one alternative, blood separation layer comprises a glass fiber matrix.

In another embodiment, an apparatus for measuring concentration of multiple analytes in a whole blood sample includes a test matrix including an elongated porous disbursement layer; a blood separation layer adjacent to the bottom surface of the disbursement layer; and at least two vertically aligned stacks spaced apart and adjacent to the bottom surface of the blood separation layer and a first one of the vertically aligned stacks includes multiple layers, the multiple layers including a reagent and a chromagen. The apparatus further includes an electrochemical testing member including a sample area; an electrode; and a counter-electrode and the electrode and counter-electrode are oriented in electrical communication with each other when a blood sample is present, and the electrode and the counter-electrode located in the sample area. The apparatus further includes a hybrid test strip holder having a top portion and a bottom portion sandwiching the test matrix there between; the top and bottom portions holding the electrochemical testing member; the top portion of the hybrid test strip holder having a sample application window exposing a top surface of the disbursement layer and the sample area, such that blood from a single sample in a lance is received in the sample area and the disbursement layer; and the bottom portion of the hybrid test strip holder having at least one test reading window through which bottom surfaces of the first and second stacks can be read.

BRIEF DESCRIPTION OF THE DRAWINGS

FIG. 10 is a top view of an electrochemical testing member;

FIG. 11 is a top view of a hybrid strip;

DETAILED DESCRIPTION

The embodiments described below are not intended to be exhaustive or to be limited to the precise forms disclosed in the following detailed description. Rather, the embodiments are chosen and described so that others skilled in the art may appreciate and understand the principles and practices disclosed herein.

DEFINITIONS

"HDL" refers to high density lipoprotein.

"LDL" refers to low density lipoprotein.

"VLDL" refers to very low density lipoprotein.

"NonHDL" refers to LDL, VLDL, and chylomicrons, as well as lipoproteins other than HDL that will react with a conventional cholesterol reaction membrane.

"PTA" refers to phosphotungstic acid.

"HDL fractionation layer" refers to a dry hybrid test strip layer selected from suitable materials and impregnated with one or more reagents such that non-HDL cholesterol (VLDL and LDL) in a fluid sample deposited on the layer are both precipitated and substantially retained within the layer, but HDLs in solution in the sample remain in solution and are able to pass through the fractionation layer.

"Plasma" refers to the non-cellular portion of blood from which cellular components such as red blood cells are excluded.

"Serum" technically differs from plasma in that it does not include fibrinogen. However, for purposes of this application, "serum" and "plasma" are sometimes used interchangeably.

Figure 1:
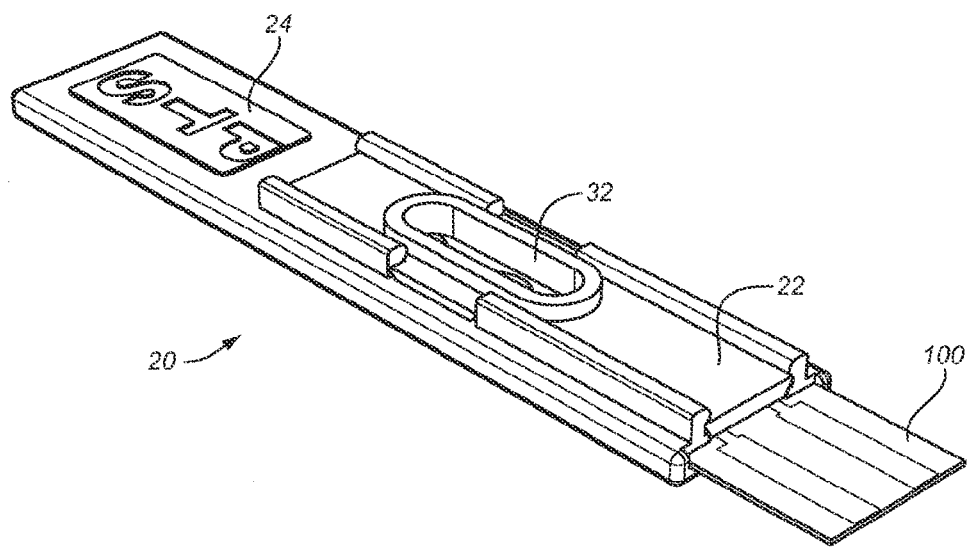
FIG. 1 is a perspective view of an embodiment of a hybrid strip.

Referring to FIG. 1, hybrid test strip 20 includes hybrid test strip holder 22. Hybrid test strip holder 22 may be formed of a variety of different materials including, but not limited to, metal and plastic. In the case of a plastic hybrid test strip holder 22, the plastic may be formed using injection molding. The hybrid test strip holder 22 includes an opening 32 for receiving a blood sample. Opening 32 is depicted as an oval-shaped opening in FIG. 1; however, alternative openings of all types of geometric shapes are possible including circles, squares, rectangles, etc. Handle 24 is depicted in FIG. 1, allowing for a user to conveniently handle the hybrid test strip using Handle 24. Handle 24 is an optional feature, however, and need not be included for the function of hybrid test strip 20. Hybrid test strip 20 includes an electrochemical testing member 100 that is integrated with the photochemical portion.

Figure 2:
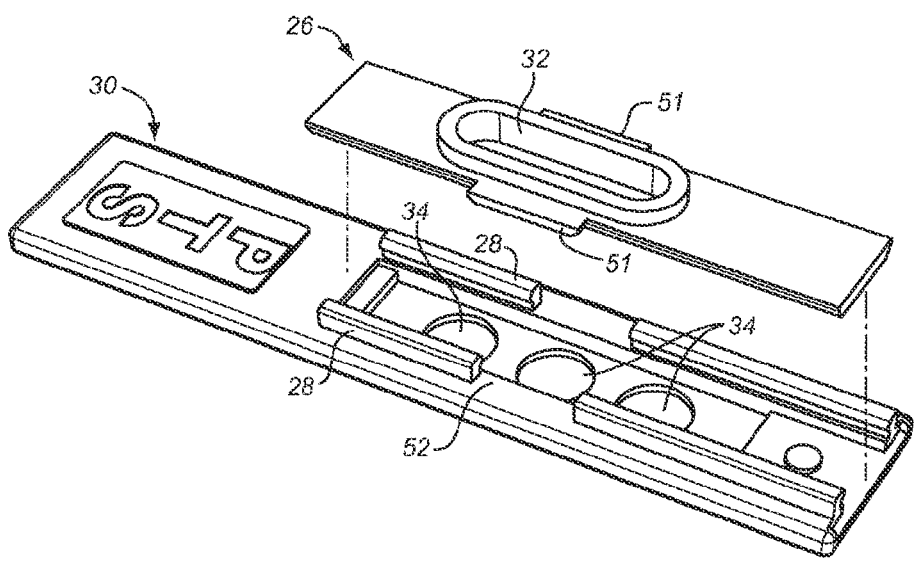
FIG. 2 is a perspective view of an embodiment of a hybrid strip where the top portion has been removed.

As depicted in FIG. 2, hybrid test strip 20 includes a top portion 26 and a bottom portion 30. The top portion includes opening 32 and the bottom portion 30 includes openings 34. Although in FIG. 2 three openings 34 are shown, various configurations of openings are possible. The openings 34 provide for a window for photometric testing of samples. Generally, the photometric testing through openings 34 is a measure of reflectance; however, other photometric testing techniques may be used including transmissivity and absorption. The number of openings corresponds to the number of samples that are subjected to photometric testing. Optionally, openings 34 can be configured with transparent windows.

Top portion 26 and bottom portion 30 fit together as shown in FIG. 2. A variety of configurations are possible for fitting the top portion 26 and the bottom portion 30 together. As shown in FIG. 2, side bars 28, 29 serve to hold the top portion 26 in place. Snap pieces 51 may be snapped on to side bars 28, 29 at grooves 52. This configuration provides a friction fit. Top portion 26 may be further secured with adhesive or simply a friction fit. In one alternative, the top portion 26 and the bottom portion 30 may be hinged or non-hinged. The non-hinged end of the top portion 26 may be held in place by a variety of locking mechanisms that will be apparent to those skilled in the art in light of this disclosure.

Figure 3:
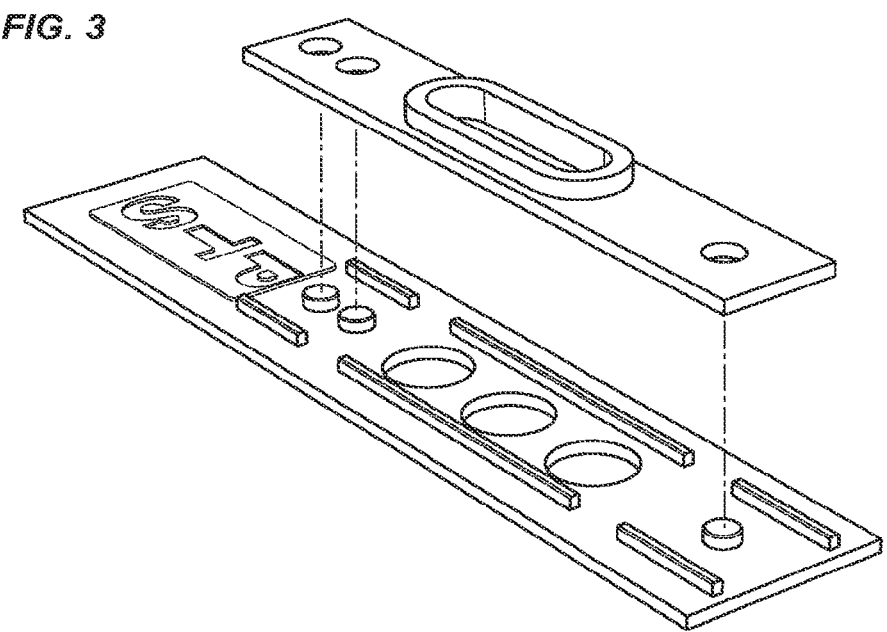
FIG. 3 is a perspective view of an alternative embodiment of a hybrid strip where the top portion has been removed.

In one alternative, shown in FIG. 3, the top portion 26 and the bottom portion 30 include a number of receptacles 50 housing a number of pegs 49 that fit via a friction fit into mating cylindrical openings 56. This type of locking mechanism keeps the distance and fit of the top portion 26 and the bottom portion 30 constant. An improper fit between the top portion 26 and the bottom portion 30 may cause irregular sample flow and result in erroneous analyte measurements due to changes in the diffusion speed and/or pattern of samples.

Figure 4:
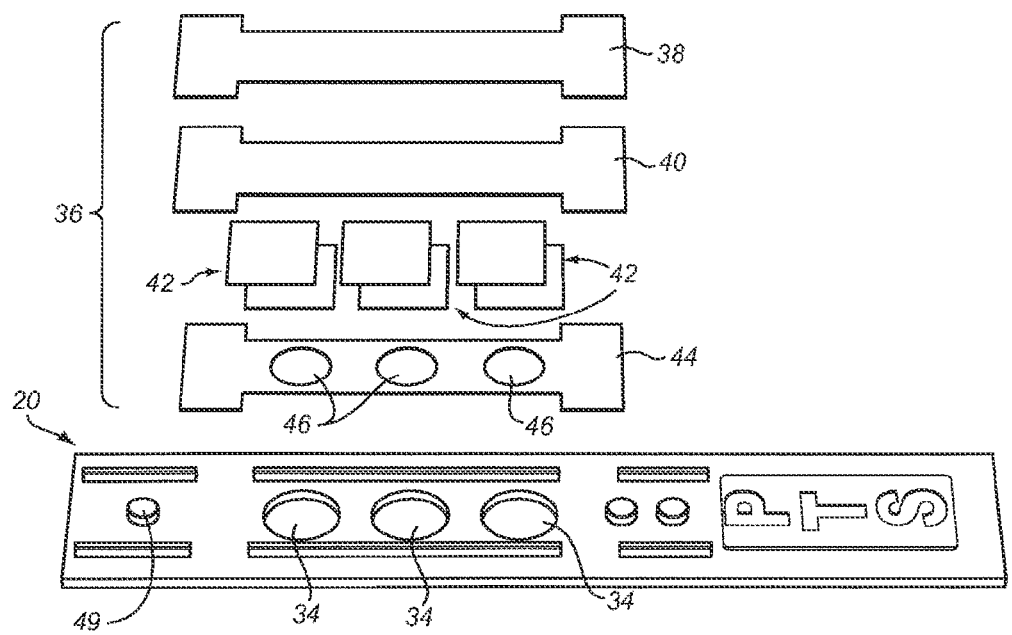
FIG. 4 is an exploded perspective view of a hybrid strip showing the layers of a test matrix.

Hybrid strip 20 is designed to provide many different types of analyte testing. A first embodiment of the hybrid strip 20 includes two types of analyte testing, photometric and electrochemical. To support photometric testing, hybrid strip 20 is configured with a test matrix 36 that includes at least one stack 42. In FIG. 4, an exploded view of test matrix 36 is shown. Test matrix 36 is made up of a top disbursement layer 38, a blood separation layer 40, stacks 42, and adhesive layer 44 having openings 46 that align with openings 34 and the bottoms of respective stacks 42 when the layers are assembled. Stacks 42 are further made up of one or more vertically aligned layers, the function and specifics of which are described in further detail below. When assembled and closed, the layers of stacks 42 and layers 38, 40, and 44 are all pressed together. Opening 32 exposes a part of the top surface of disbursement layer 38, and openings 34 and 46 expose the bottom surface of bottom portion 30 and the bottom layers of stacks 42.

In another embodiment, the test strip may include multiple different test areas, retention areas, and/or distribution areas (together referred to as test elements and the strip referred to as a multi-test element strip. Test areas may include as mentioned about electrochemical and photometric test areas and further may include other type of test areas, including liquid test areas, gel test areas, and gas interface test areas. Retention areas may include areas established for holding blood for a set period of time before testing and areas for capturing a sample of blood for later usage. Distribution areas may include areas to which a testing device may be hooked up to siphon a portion of the sample for testing within a testing device.

A test strip with multiple different test areas, retention areas, and/or distribution areas (together referred to as test elements) configuration generally has a spreading layer. The spreading layer functions to spread the sample so that it can reach the various test area, retention areas, and distribution areas that are included in the strip. The time of absorption for the spreading layer set in proportion to the amount of spreading desired. The time of absorption may be modified by treating the spreading layer with materials impervious to liquid and by changing the weave of the spreading layer. More spreading will be desired based on the number test elements in the strip. Also the size of the sample anticipated may limit the number of test elements that may be included.

Continuing with the above multi-test element strip, sample absorbed into the spreading layer is generally be used to bring a sample to a test stack, composed of testing layers. The testing layers may ultimately be analyzed based on photometric or electrochemical techniques. Alternatively, absorbed sample may be transferred to a gel testing area. During spreading (and absorption), part of the sample may be captured by capillary tubes or other mechanisms, such at absorbent materials. These portions of the sample may be transferred to other test elements. In one example, that is explained further herein, a capillary tube carries a portion of the sample to be tested electrochemically. Alternatively, the sample may be deposited in a storage retention area. This storage retention area is designed to keep a historical sample record and may be sealed by the user depressing a tab on the test strip that closes off the storage retention area. Alternatively, a delay retention area may be used. The sample portion may be transferred to the delay retention area using the above described techniques. In the delay retention area includes a slow absorbing layer that slows the process of the sample portion to the test area. Such a technique may be used to test for the oxygen absorption rate of a sample, where one sample is tested immediately and another is delayed by the delay retention area. Such a delay retention area may be used whenever timing is important in testing. Alternatively, a portion of the sample may be transferred to a distribution area. When the test strip is inserted into a test device, sample may be transferred to the distribution area, for example by a vacuum suction. Due to the usage of the spreading layer a test strip may be configured with numerous alternative test elements.

Figure 5:
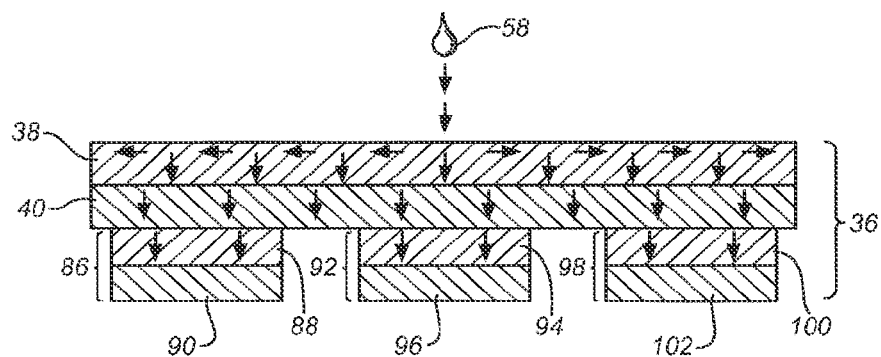
FIG. 5 is cross-section view of a test matrix.
Figure 6:
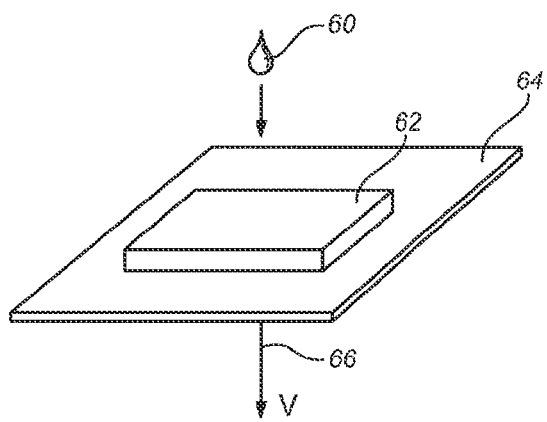
FIG. 6 is a perspective view illustrating a vertical flow scheme utilized by stacks.

Continuing with the hybrid strip example, referring to FIG. 5, the individual layers and the diagnostic chemistries of matrix 36 can be appreciated. The top layer 38 of matrix 36 is a disbursement or spreader layer capable of efficiently spreading the blood sample 58 through its entire length such that the blood sample 58 is deposited vertically to the next layer over the entire length of layer 38 (see reference arrows in FIG. 5). For example, a mesh, such as polyester mesh, works well for single hybrid test strips, such as those disclosed in U.S. Pat. No. 5,597,532. However, when such mesh is used in an attempt to spread blood across an elongated matrix such as matrix 36, the blood inevitably is drawn to the layer below the mesh (layer 40) before it spreads to the outer ends of layer 38. If this occurs, no blood will be drawn into the electrochemical testing member 100. Therefore, a lower permissively spreading layer may be required to integrate the testing mechanisms.

The problem of blood being drawn into layer 40 from layer 38 presented a serious design hurdle. The problem is caused in large part by layer 40, which is a glass fiber depth filter that is adjacent to and in contact with layer 38. When in contact with layer 38, layer 40 exerts a wicking effect on layer 38, tending to draw blood into layer 40 at its center before the blood can sufficiently spread to the ends of the elongated disbursement layer 38. A sufficient blood sample is delivered to the middle of layer 40, but not to its ends. This results in unpredictable and uneven deposition of the blood filtrate onto stacks 86 and 98 and can result in blood not being drawn into the electrochemical testing member 100, which in turn results in unpredictable test results.

Remarkably, the disbursement or spreader layer 38 spreads blood sample 58 (FIG. 5) efficiently and sufficiently throughout the entire length of layer 38 as shown by the reference arrows—even with layer 40 being in constant contact therewith. This is a significant achievement, in that it allows a multi-analyte dry phase hybrid test strip that uses only a single 35 microliter sample of blood yet has no moving parts.

Without wishing to be tied to any specific theory, it is believed that layer 38 operates by a two-stage mechanism, although it should be understood that the steps may not occur sequentially, but instead may occur simultaneously to a certain degree. In the first step, blood sample 58 (FIG. 5) spreads laterally within layer 38; in the second step, the sample is deposited vertically onto layer 40. Again, it should be expected that the second step may begin at the central portion of layer 38 before it occurs at the ends of layer 38; but there are inarguably two functions occurring, the first being spreading the blood sample throughout the entire length of layer 38, and the second being delivering the blood sample uniformly to the next layer over the entire length of layer 38.

Surprisingly, it has been found that layers used as conjugate pads in pregnancy test kits perform quite well as layer 38. Layer 38 is an open cell layer capable of rapidly and effectively spreading the fluid sample. One suitable material for layer 38 is available under the name Accuflow Plus-P available from Schleicher & Schuell Bioscience, Inc., Keene, N.H. Another suitable material for layer 38 is available under the name Accuwik™ manufactured by Pall Corporation, East Hills, N.Y. Layer 38 may be constructed of hydroxylated polyester. The fiber surfaces have been modified to be inherently and permanently water-wettable. Layer 38 provides an excellent wicking rate and high volume retention capability, which allows the blood to spread laterally across the entire length of the layer. U.S. patent application Ser. No. 10/663, 555 entitled "Test Strip And Method For Determining LDL Cholesterol Concentration" filed on Sep. 16, 2003, and published Jul. 1, 2004 under U.S. Patent Application Publication No. 2004/0126830 is hereby incorporated by reference.

Generally, layer 38 must provide extremely consistent flow characteristics, be intrinsically water-wettable, and exhibit sufficient volume retention capability such that the sample spreads throughout the entire length of the layer, even though another layer such as layer 40 that acts as a wick is positioned in constant contact therebelow. It is anticipated that other layers possessing the above characteristics would work for layer 38. Furthermore, see the discussion below of the necessity to enable flow to the electrochemical testing member 100.

As will become clearer with reference to the discussion below, substantial lateral spreading occurs only in disbursement layer 38 of matrix 36. In the remaining layers, the net direction of fluid flow is believed to be substantially vertical, or normal, to the plane of the layers. For example, with reference to FIG. 7, fluid sample drop 60 is deposited onto layer 62 (which could be blood separation 10 on layer 40 or one of the layers from one of stacks 42). Layer 62 defines a plane 64 that is substantially parallel therewith. Transfer of fluid through layer 62 is normal or perpendicular to plane 64, or in the direction of vector V, shown at reference numeral 66. Thus, there is no substantial migration of fluid from one side of layer 62 to the other. Fluid flow is through layer 62, not across it.

In this connection, it should also be appreciated that, even though lateral spreading of a fluid sample occurs in layer 38, the sample application window 32 is substantially vertically aligned with or at least partially projects over the test reading windows 34 as shown in FIG. 4. The length of hybrid test strip 20 is governed by the peripheral dimension of the stacks 42. As shown in FIG. 4, test stacks 42 define a lengthwise periphery "P", whereas test application window 32 defines a lengthwise periphery "p". The test window 32 can be positioned within the periphery P defined by stacks 42 as shown in FIG. 4. This allows a more compact hybrid test strip than in a lateral flow device, wherein test window 32 would be positioned outside of the lengthwise periphery P, thus requiring a longer strip.

Figure 7:
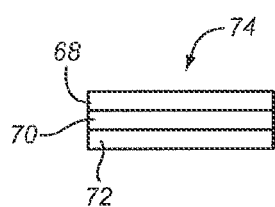
FIGS. 7-9 depict various embodiments of "vertically aligned" layers.
Figure 8:
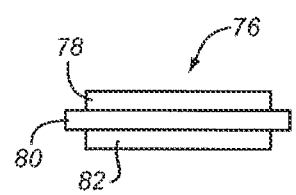
Figure 9:
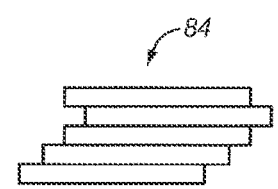

Furthermore, because lateral flow does not occur in any of the layers other than layer 38, the layers can be "vertically aligned", as shown in FIGS. 7-9. With particular reference to FIG. 7, equal size layers 68, 70, and 72 of stack 74 are aligned directly over one another. While such direct alignment may be advantageous because it is most compact, it should be understood that other minor variations of vertical alignment are within the scope of this disclosure. For example, FIG. 9 depicts a stack 76 in which middle layer 80 is larger than and protrudes slightly from layers 78 and 82. Similarly, stack 84 shown in FIG. 9 is depicted as crooked, wherein the layers thereof are not placed directly over one another.

The hybrid strip 20 has an integrated electrochemical testing mechanism. The ability of the hybrid strip to perform both sets of tests is due in part to the initial spreading of the sample, such that the electrochemical testing member can receive a sufficient sample for testing. Electrochemical blood testing generally refers to a procedure where the resistance, potential (charge), or voltage of a sample is measured, and includes coulometric, voltammetric, ampherometric, and potentiometric techniques. In coulometry, the amount of matter transformed during an electrolysis reaction is determined by measuring the amount of electricity (in coulombs) consumed or produced. The amount of electricity produced may be correlated to the analyte concentration. In voltammetry, information about an analyte is obtained by measuring the current as the potential is varied. In ampherometry, the resistance of an undercurrent flow is measured and this resistance is correlated to analyte concentration. In potentiometry, the potential of a sample under no current flow is measured. The measured potential then may be used to determine the analytical concentration of some components of the analyte gas or solution. In the present application, although the electrochemical mechanism employed by the hybrid strip 20 may be described in relation to a specific testing technique, any of these testing techniques may be utilized with small modifications that will be apparent to those skilled in the art in light of this disclosure.

Referring to FIGS. 9 and 10, electrochemical testing member 100, shown in FIG. 5, is designed to fit between top portion 26 and bottom portion 30 such that the end of testing member 100 extends beyond the area of the hybrid test strip defined by top portion 26 and bottom portion 30. The electrochemical testing member 100 has a sample chamber 110 into which the blood sample to be tested is transferred. Electrode 115 and counter-electrode 120 extend into sample chamber 110. Sample chamber 110 is configured such that electrode 115 and counter-electrode 120 will be immersed in the sample. Sample chamber 110 may be a tube with capillary properties. When a drop of blood is placed in window 32, the blood spreads across disbursement layer 38. When the blood comes into contact with sample chamber 110, the capillary effect pulls some of the sample into sample chamber 110. The sample chamber 110 receives blood by virtue of the initial spreading, which allows a test sample area to receive sufficient blood to perform the required testing. In one alternative, the initial permissivity of the spreading layer (layer 38) is reduced such that sufficient blood can reach the sample chamber. A cap 130 fits over electrode 115, counter-electrode 120, and sample chamber 110 resulting in an enclosed tested area, open only at the point at which the sample deposited in window 32 enters.

In one embodiment, in order for the spreading layer (layer 38) to sufficiently spread the blood initially, but then allow absorption, the layer may be treated or woven more tightly to enable initial spreading. In an alternative embodiment, treatment may include adding sorbitan monooleate and/or polyethoxylated hydrogenated castor oil with a low percentage coating based on weight. In one embodiment, the coating level may be 0.01-0.1%. The coating level may be based at least in part on the surface area of the spreading layer; the larger the surface area, the more of a coating will be needed in order to allow for initial spreading to the electrochemical testing member.

In one embodiment, the sample chamber 110 may include a loosely woven material that quickly absorbs liquid in contrast to the spreading layer. The electrodes may be positioned in the loosely woven material such that when the material absorbs the sample, the electrodes are in contact with the sample. In one alternative, the loosely woven material is electrochemically neutral and does not greatly affect the electrochemical testing procedure. The loosely woven material may include loosely formed cellulosic fibers and may also contain superabsorbent polymer fibers to improve the absorbent capacity. The term "superabsorbent polymer" (or "SAP") generally refers to materials which are capable of absorbing and retaining at least about 10 times their weight in body fluids under a 0.5 psi pressure. Such superabsorbent polymers include crosslinked hydrophilic polymers, such as polyvinyl alcohols, polyethylene oxides, crosslinked starches, guar gum, xanthan gum, and the like. One example of a commercially available SAP material is AQUAKEEP SA-70, available from Sumitomo Seika Chemicals Co., Ltd. In usage, the loosely woven material may allow for the sample chamber to be larger and less bounded since the loosely woven material may assist in the flow of the sample. In yet another embodiment, the sample chamber 110 may also not employ the capillary effect, but instead simply rely to the ability of the spreading layer to resist the penetration of the sample sufficiently for the sample to spread into the sample chamber 110.

Connections 121, 122 extend from electrode 115 and counter-electrode 120 to leads 123, 124. Referring to FIG. 11, opening 125 is designed to fit onto rod 49 to allow for a friction fit for the electrochemical testing member 100. Electrochemical testing member 100 is also held in place by top portion 26 and bottom portion 30.

In the pictured embodiment, electrode 115 and counter-electrode 120 are formed such that counter-electrode 120 substantially surrounds electrode 115; however, such precise configuration is not required. The electrodes may be oriented in a variety of arrangements, as long as they are in electrolytic contact with the sample. In one alternative, electrode 115 and counter-electrode 120 are separated by a distance of 0.01-1 mm. The distance separating the electrodes and the sample size may impact the precision of analyte measurements.

For the electrodes to measure an analyte, a reagent must be introduced. A layer of enzymatic reactants overlays the electrodes and provides a substrate for the sample. The reactant used is dependent on the type of electrochemical test being conducted and the analyte being tested for. Some examples of enzymatic reactants are described below. A variety of reagents will be apparent to those skilled in the art in light of this disclosure.

To perform testing, the hybrid test strip is inserted into a testing device with optical and electrochemical testing mechanisms. Optical testing mechanisms involve a light source and a light sensor. The light sensor senses the light reflected from the samples through openings 34. The measured light level is processed by an analog-to-digital (A/D) converter and fed to a microprocessor that performs the calculation to determine the corresponding analyte level. The electrochemical testing mechanism is performed according to a similar procedure. The electrical property corresponding to the electrochemical method is tested for (voltage, resistance, current) and then converted by an A/D converter and processed by a microprocessor to determine the corresponding analyte level.

The leads 123, 124 of the electrochemical testing member 100 are designed to line up with leads inside of the testing device such that the needed electrical stimulus can be applied and the result measured (in some cases, no electrical stimulus is applied). This measurement is converted by an A/D converter and processed by a microprocessor to determine the corresponding analyte level.

Users receive the hybrid testing strip 10 as a complete testing strip, requiring the user to place a blood sample in window 32 and place the hybrid testing strip 10 into a testing device. In one alternative, the hybrid testing strip comes completely assembled and the analytes it is configured to test for is preset. In another alternative, the electrochemical testing member 100 is interchangeable. In this alternative, a hybrid strip 10 with preset photochemical testing stacks may receive an electrochemical testing member selected by the user. Therefore, at the time of usage the user may customize the hybrid strip to receive a single blood sample and test for multiple analytes.

The electrochemical testing member 100 may be inserted by separating top portion 26 and bottom portion 30 (which may be hinged, see above) and fitting opening 125 on to rod 49. Alternative insertion and locking techniques may be utilized, which will be apparent to those skilled in the art.

Figure 21:
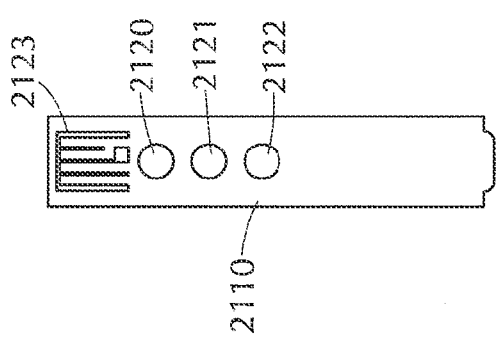
FIG. 21 shows an alternative embodiment of a hybrid strip.

FIG. 21 shows another embodiment of a hybrid strip 2110. In this version, printed electrodes 2123 are adjacent to test windows 2120, 2121, 2122. Printed electrodes 2123 may be integrated with the strip in a variety of fashions including, but not limited to, forming the electrodes as part of the plastic. This may be accomplished by printing the electrodes directly on the plastic. Alternatively, the hybrid strip may include a cut out for receiving the electrodes or may include a cut-away access window, such that when the strip is inserted in a meter, the electrodes may be contacted by the meter and measurements may be performed. In this case, a subject may use a lance to retrieve blood and then a sample may be added for use in the spreading layer and then the residual amount in the lance will typically be enough blood to activate the electrochemical strip (0.5 microliters in many cases). This allows for a user to apply blood to both areas with the use of a single lance and blood sample.

Multiple alternatives are available for the blood to reach the electrodes. In some embodiments, the electrodes may be immediately adjacent to the top spreading layer. In other embodiments, a stack below the spreading layer may bring blood to the electrodes. In some embodiments, the stack bringing blood to the electrodes may be simply a very porous pass through. In other embodiments, the layers may filter out red blood cells, improving the performance of the electrochemical test.

Figure 22:
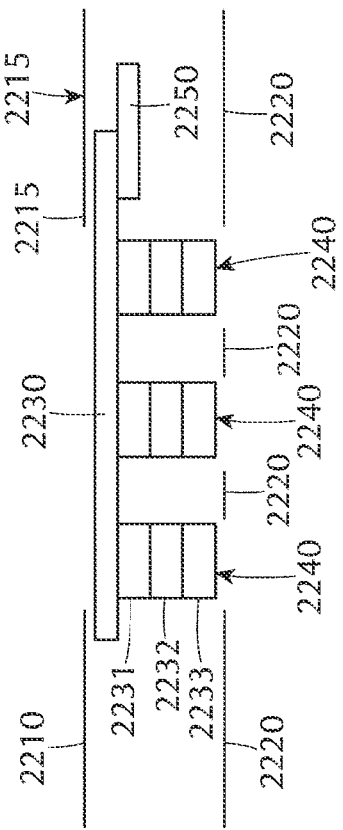
FIG. 22 shows an illustrative drawing of a cross section of an alternative embodiment of a hybrid strip.

FIG. 22 shows one conceptual drawing of an embodiment of a hybrid strip (a cross-sectional view). In this strip, spreading layer 2230 is in contact with electrodes 2250. Blood from spreading (or disbursement) layer 2230 spreads to each of the three stacks and down through layers 2231, 2232, 2233. Blood also spreads to a sample area in the electrochemical portion where the electrodes are located. The amount of contact between the disbursement area and the electrochemical sample area may be optimized so that the amount of blood delivered is optimal. The more of the electrochemical sample area and surrounding area that contacts the disbursement layer, the more blood will be drawn to the electrochemical sample area through what is thought to be surface tension principles. A colorimetric reaction may take place in the bottom layer 2233 and then be ready through sample windows 2240. The features of the body of the strip are visible and include body portions 2210, 2220, and 2215. A window or cut-away may be employed to provide access to the electrochemical portion when inserted in a meter. In an alternative, a stack of layers may be located between spreading layer 2230 and electrodes 2250. This is thought to be somewhat less optimal, since a greater volume of blood may be required. In alternatives, less than three colorimetric stacks may be used.

One embodiment of the present invention includes a lipid panel plus ampherometric glucose. The lipid panel tests for Total Cholesterol, HDL Cholesterol, and Triglycerides. The enzymatic reactions for the lipid panel may be characterized as shown below:

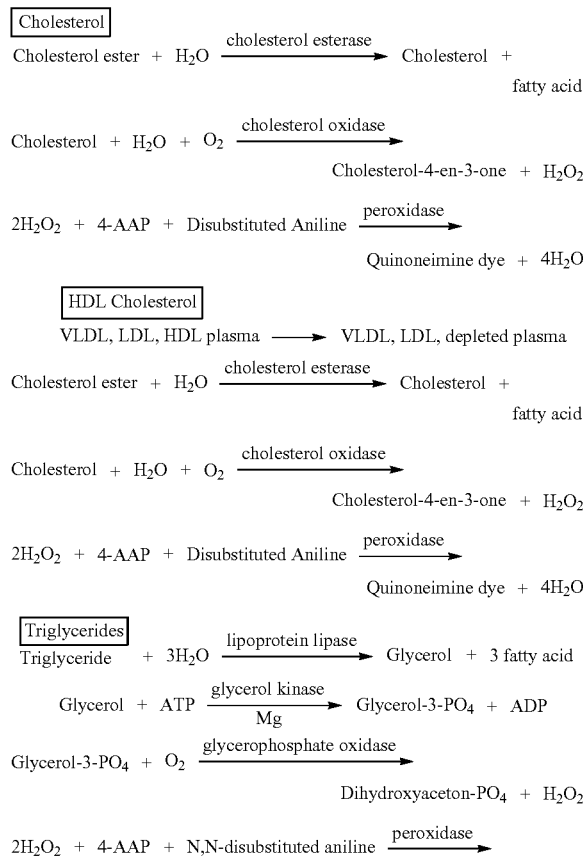

HDL Measurement Stack

With reference to FIG. 5, middle stack 92 having layers 94 and 96 is adjacent to and in fluid communication with the bottom side of layer 40. Stack 92 takes fluid from layer 40 and produces a colored response in reaction layer 90 that is proportional to the concentration of HDL cholesterol. Layer 40 does not separate 100% of red blood cells. Instead, about 20% of red blood cells escape to layers 88, 94, and 100. Thus, layers 88, 94, and 100 separate and retain residual blood cells passed to them from layer 40.

As noted above, the prior art generally teaches that two layers and two associated process steps are necessary to precipitate and separate non-HDLs from plasma. According to the prior art approach, precipitation of non-HDLs is carried out in the first layer, and the precipitants then pass through this first layer to a second layer. In the second layer, the precipitants' migration is slower than that of plasma, and the plasma reaches the test membrane before the precipitants. See, e.g., U.S. Pat. Nos. 5,426,030; 5,580,743; 5,786,164; 6,171,849; 6,214,570; 5,451,370; 5,316,916; 5,213,965; and 5,213,964. In contrast, as disclosed herein, separation of non-HDLs from HDLs can be achieved in a single substantially uniform layer 94.

Further, it has been found that precipitation and separation take place in a direction that is substantially normal to the plane established by layer 94. That is, while fluid movement occurs in all directions within layer 94, there is no significant net tangential migration of fluid from one side of layer 94 to the other. Indeed, this embodiment does not incorporate or rely on different migration rates of plasma and precipitated non-HDLs across layer 94. This is because fluid transport is through layer 94, not across it.

Many suitable materials can be used for layer 94, such as filter paper or cellulose acetate in combination with glass fibers. One suitable membrane for layer 94 is CytoSep® grade 1660 membrane, 12.9 mils thick, available from Pall Corporation, East Hills, N.Y. Another suitable membrane for layer 94 is paper grade 595, 0.180 mm (7.1 mil) thick, available from Schleicher & Schuell Bioscience, Inc., Keene, N.H. Further, layer 94 is substantially uniform throughout or symmetric. That is, while the matrix of layer 94 includes pores of different sizes, the matrix is consistent throughout the entire layer. Layer 94 is impregnated with the solution described hereinbelow in the examples.

Total Cholesterol Measurement Stack

With further reference to FIG. 5, end stack 86 is spaced from middle stack 92 and is adjacent to and in fluid communication with layer 40. Stack 86 takes fluid from layer 40 and produces a colored response in reaction layer 90 that is proportional to the concentration of total cholesterol in sample 58. Stack 86 also includes a blank or spacer layer 88 whose main purpose is to maintain the relative thickness of all stacks approximately the same and, in so doing, improves overall compression exerted upon matrix 36 by top portion 26 and bottom portion 30 of strip holder 22. Blank layer 88 also retains residual blood cells passed to it from layer 40. For purposes of this specification, the term "blank layer" refers to a layer such as layer 88 whose main purpose is to maintain all stacks at substantially the same thickness. Blank layer 88 is not loaded with any reagents, but may be impregnated with a wetting agent to improve fluid flow or may be impregnated with a chromogen in applications wherein two test membranes are employed. A specific functioning example of a total cholesterol measuring stack 86 is set forth in the Examples hereinbelow.

Triglycerides Stack

With further reference to FIG. 5, stack 98 is spaced from stack 92 and is adjacent to and in fluid communication with layer 40. Stack 98 takes plasma from layer 40 and produces a colored response in reaction layer 102 that is proportional to the concentration of triglycerides in sample 58. Stack 98 also includes a blank or spacer layer 100 that, in this embodiment, is the same as blank layer 88. An example of a triglycerides measuring stack 98 is set forth in the Examples hereinbelow.

It should be understood that once HDL concentration, total cholesterol, and triglycerides concentrations are determined from stacks 86, 92, and 98, respectively, the concentration of LDL cholesterol can be calculated by the well-known relationship:

LDL cholesterol=total cholesterol−triglycerides/5−HDL cholesterol.

A simple linear equation like that above can easily be programmed into the instrument that optoelectronically reads the hybrid test strips, thus providing concentration of an additional analyte that was not measured directly.

Ampherometric Glucose

The ampherometric glucose test is performed by the electrochemical testing member 100. A mediator enables the testing of the glucose level. An enzyme such as glucoseoxidase (or Hexokinase or other enzyme specific for glucose) may be used to create cuprous oxide. A voltage is applied to the sample and the current is detected. The current detected is proportional to the concentration of glucose.

The use of ampherometric glucose detection systems may allow for the interference of ascorbic acid, acetaminophen, and uric acid to be minimized. One approach for limiting these interferents is to utilize a selectively permeable membrane (permeable only to hydrogen peroxide, a result of the enzymatic reaction). Another approach includes selective electrocatalysis. Platinum and horserasdish peroxidase may be used for electoreduction. These interferent limiting mechanisms are applicable to testing for other analytes and should not be construed as limited to glucose.

Examples of the layers that may form the test matrix are as follows:

Example 1

Solution for Impregnation of Blood Separation Layer 40

The following impregnation solution was used:

| | |
|---|---|
| Deionized water | 800.00 mL |
| D-Sorbitol | 75.00 gm |
| Sodium Chloride | 10.00 gm |
| Adjust the volume to 1 liter with deionized water. | |

Example 2

Impregnation of Blood Separation Layer 40 with Solution of Example 1

A fiberglass membrane (Ahlstrom Tuffglass™) 6.0" (inches) wide was submersed in a re-circulating bath of the impregnation solution of Example 1 at a rate of 0.5 ft/min. It then entered a tunnel of blowing warm air (98° to 106° Fahrenheit) and low humidity (<5% relative humidity (RH)) to completely dry. It was then slit into 0.80" (inch) strips in preparation for assembly.

Example 3

Impregnation of Blood Separation Layer 40 with Solution of Example 1

A fiberglass membrane (Schleicher and Schuell 33) 6.0" (inches) wide was submersed in a re-circulating bath of the impregnation solution of Example 1 at a rate of 0.5 ft/min. It then entered a tunnel of blowing warm air (98° to 106° Fahrenheit) and low humidity (<5% RH) to completely dry. It was then slit into 0.80" (inch) strips in preparation for assembly.

Example 4

Solution for Impregnation of HDL Fractionation Membrane (Layer 94)

The following impregnation solution was used:

| | |
|---|---|
| Deionized water | 800.00 mL |
| Magnesium Sulfate | 5.00 gm |
| Phosphotungstic Acid | 45.00 gm |
| Sorbitol | 10.00 gm |
| Adjust pH with NaOH or HCl | pH 6.40-6.60 |
| Adjust the volume to 1 liter with deionized water. | |

Example 5

Impregnation of Layer 94 with Solution of Example 4

A synthetic fiber composite media (Pall CytoSep™ grade 1660) 12.9 (mils) thick, 5.90" (inches) wide was submersed in a re-circulating bath of impregnation solution at a rate of 0.5 ft/min. It then entered a tunnel of blowing warm air (98° to 106° Fahrenheit) and a low humidity (<5% RH) to completely dry. It was then slit to 0.20" (inch) strips in preparation for assembly.

Example 6

Impregnation of Layer 94 with Solution of Example 4

A synthetic fiber composite media (Pall CytoSep™ grade 1661) 7.1 (mils) thick, 6.0" (inches) wide was submersed in a re-circulating bath of impregnation solution at a rate of 0.5 ft/min. It then entered a tunnel of blowing warm air (98° to 106° Fahrenheit) and a low humidity (<5% RH) to completely dry. It was then slit to 0.20" (inch) in preparation for assembly.

Example 7

Impregnation of Layer 94 with Solution of Example 4

A general purpose paper (Schleicher and Schuell 595) 6.0" (inches) wide was submersed in a re-circulating bath of impregnation solution at a rate of 0.5 ft/min. It then entered a tunnel of blowing warm air (98° to 106° Fahrenheit) and a low humidity (<5% RH) to completely dry. It was then slit to 0.20" (inch) strips in preparation for assembly.

Example 8

Solution for Impregnation of Triglycerides Reaction Layer (Layer 102)

The following impregnation solution was used:

| | |
|---|---|
| Deionized water | 800.00 mL |
| Triton X-100 | 1.00 gm |
| CHAPS | 0.70 gm |
| Klucel Citrate Foundation | 575.20 gm *see below |
| 10% Gantrez AN139 | 20.80 gm |
| Calcium Chloride, Anhydrous | 0.20 gm |
| Sucrose | 25.20 gm |
| Na2ATP | 32.00 gm |
| Adjust pH with NaOH or HCl | pH 5.70 +/− 0.10 |
| MAOS | 6.25 gm |
| G3P Oxidase | 250.00 kU |
| Peroxidase | 750.00 kU |
| Lipoprotein Lipase | 625.00 kU |
| Glycerol Kinase | 358.40 kU |
| 4-amino antipyrine | 5.55 g |
| Deionized water | 800.00 mL |
| Sodium Citrate | 20.60 gm |
| Citric Acid Monohydrate | 6.30 gm |
| Magnesium Chloride | 1.43 gm |
| BSA Std. Powder | 20.00 gm |
| Sodium Benzoate | 2.0 gm |
| Klucel EXF | 10.00 gm |
| Adjust pH to 5.5-5.7 | |
| Adjust the volume to 1 liter with deionized water. | |

*Klucel Citrate Foundation

Example 9

Impregnation of Triglyceride Reaction Layer 102 with Solution of Example 8

A nylon membrane (Pall Biodyne A™) 0.45 11 m pore size, 6.0" (inches) wide was submersed in a re-circulating bath of impregnation solution at a rate of 1.0 ft/min. It then entered a tunnel of blowing warm air (98° to 106° Fahrenheit) and a low humidity (<5% RH) to completely dry. It was then slit to 0.20" (inch) strips in preparation for assembly.

Example 10

Solution for Impregnation of Cholesterol Reaction Layers (Layers 90 and 96)

The following solution was used to impregnate layers 90 and 96:

| | |
|---|---|
| Deionized water | 200.00 mL |
| Triton X-100 | 0.77 gm |
| Cholesterol Foundation | 532.00 gm *see below |
| BSA Std. Powder | 13.88 gm |
| 10% Gantrez (w/v) | 95.61 gm |
| CHAPS | 19.82 gm |
| Sucrose | 37.01 gm |
| Adjust pH with NaOH or HCl | pH 5.00 + 1-0.10 |
| Potassium Ferocyanide | 0.11 gm |
| TOOS | 0.37 gm |
| MAOS | 4.63 gm |
| Cholesterol Oxidase | 74.00 kU |
| Peroxidase | 231.30 kU |
| Cholesterol Esterase | 240.60 kU |
| 4-Amino Anti-Pyrine | 4.16 gm |
| Adjust the pH if necessary to 5.3-5.5 | |
| Adjust the volume to 1 liter with deionized water. | |
| Deionized water | 800.00 mL |
| Sodium Citrate Dihydrate | 30.00 gm |
| PVP K-30 | 60.00 gm |
| Benzoic Acid | 2.00 gm |
| BSA Std. Powder | 4.00 gm |
| EDTA, disodium dehydrate | 1.47 gm |
| Adjust pH with NaOH or HCL | pH 5.40-5.60 |
| Adjust the volume to 1 liter with deionized water. | |
| Catalase | 0.50 kU |

*Cholesterol Foundation

Note:
Even though the same impregnation solution is used for layers 90 and 96, the result obtained in layer 90 is proportional to the concentration of HDL cholesterol (since nonHDLs have been removed), whereas the result obtained in layer 96 is proportional to the concentration of total cholesterol.

Example 11

Impregnation of Cholesterol Reaction Layers (Layers 90 and 96)

A nylon membrane (Pall Biodyne A™) 0.45 μm pore size, 6.0" (inches) wide was submersed in a re-circulating bath of impregnation solution at a rate of 1.0 ft/min. It then entered a tunnel of blowing warm air (98° to 106° Fahrenheit) and a low humidity (<5% RH) to completely dry. It was then slit to 0.20" (inch) in preparation for assembly.

Example 12

Disbursement Layer 38

A polyester membrane (Accuwik™, Pall Corporation) 13.0-14.0 mils thick, 6.0" (inches) wide is slit to 0.8" wide and put on reels with a 3.0" core in preparation for assembly.

Example 13

Disbursement Layer 38

A polyester membrane (Accuflow Plus-P™, Schleicher & Schuell) 13.0-14.0 mils thick, 6.0" (inches) wide is slit to 0.8" wide and put on reels with a 3.0" core in preparation for assembly.

Example 14

Adhesive Layer 44

A support material with adhesive (G&L 187) is slit to 0.8" (inch) wide, then placed in a hole punching die to punch 3 (three) 0.140" diameter holes, 0.215" apart vertically and 0.378" horizontally and put on reels with a 3.0" core in preparation for assembly.

Example 15

Assembly of Test Matrix 36 and Holder 22

All materials listed in examples 1-14 are placed upon a layering machine which consolidates the pre-slit membranes in a stacked format consisting of:
Disbursement layer 38
Blood Separation Layer 40

HDL fractionation layer 88
Untreated layers 94/100
Cholesterol Reaction Layers 90/96
Triglycerides Reaction Layer 102
Adhesive Layer 44

The hybrid test strip assembled as just described measures concentrations of HDL, total cholesterol, and triglycerides. As discussed above, layers 90, 96, and 102 are aligned over holes 46 in support layer 44, which in turn are aligned over openings 34 in the bottom portion 30 of hybrid test strip holder 22. A blue color proportional to the concentration of the respective analyte can be seen in each of the respective openings 34.

It is envisioned that support layer 44 could be removed in commercial embodiments, as the support layer's function is to hold the other layers in place until the strips are assembled.

Example 16

Calibration Curves

Several whole blood samples of known concentrations of HDL, total cholesterol, and triglycerides were tested by:
1. Applying a 35-40 microliter sample to opening 32 of hybrid test strips 20; and
2. Reading reflectance from the blue color on reaction layers (as seen through 35 openings 34) on a portable whole blood analyzer (BioScanner Plus™ instrument, Polymer Technology Systems, Indianapolis, Ind.).

Figure 12:
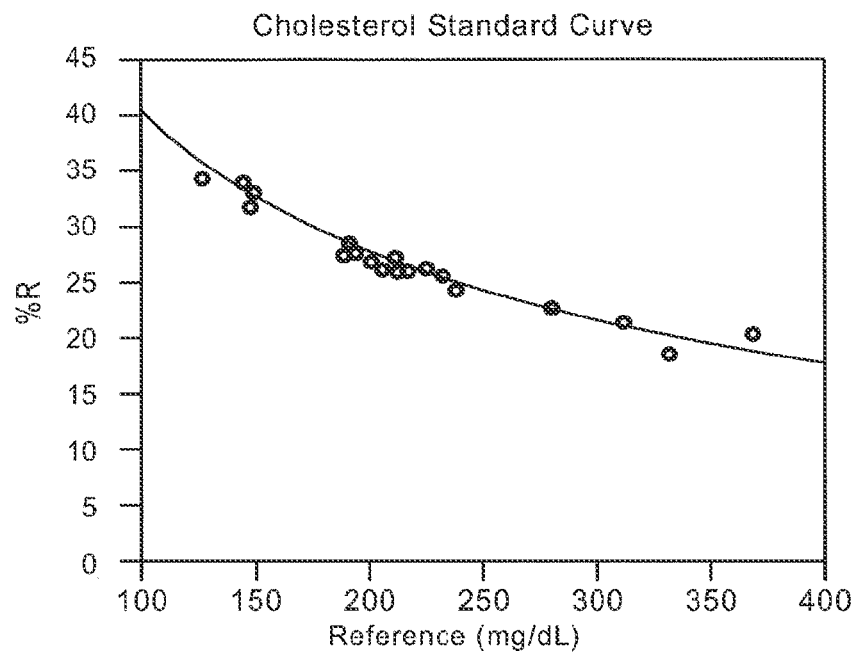
FIGS. 12-14 illustrate standard curves for cholesterol, HDL, and triglycerides, respectively.
Figure 13:
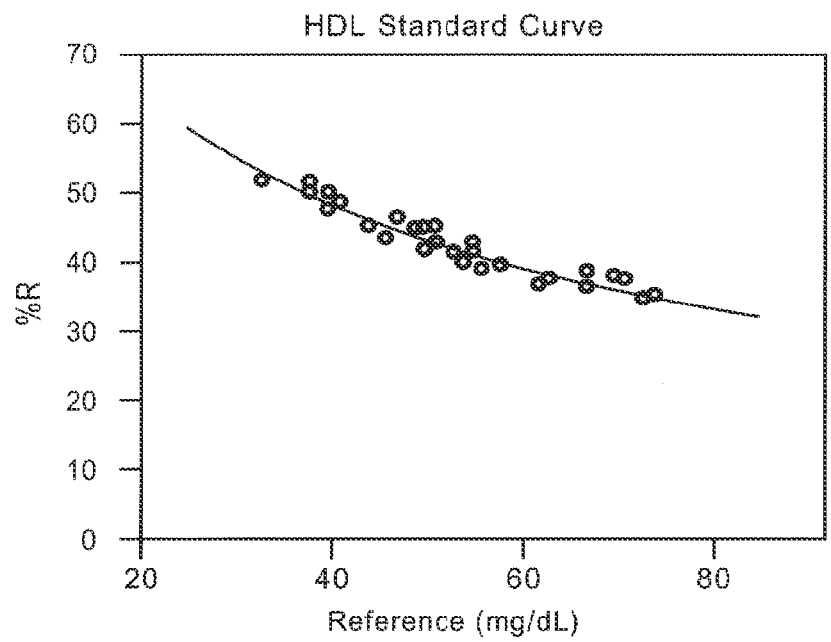
Figure 14:
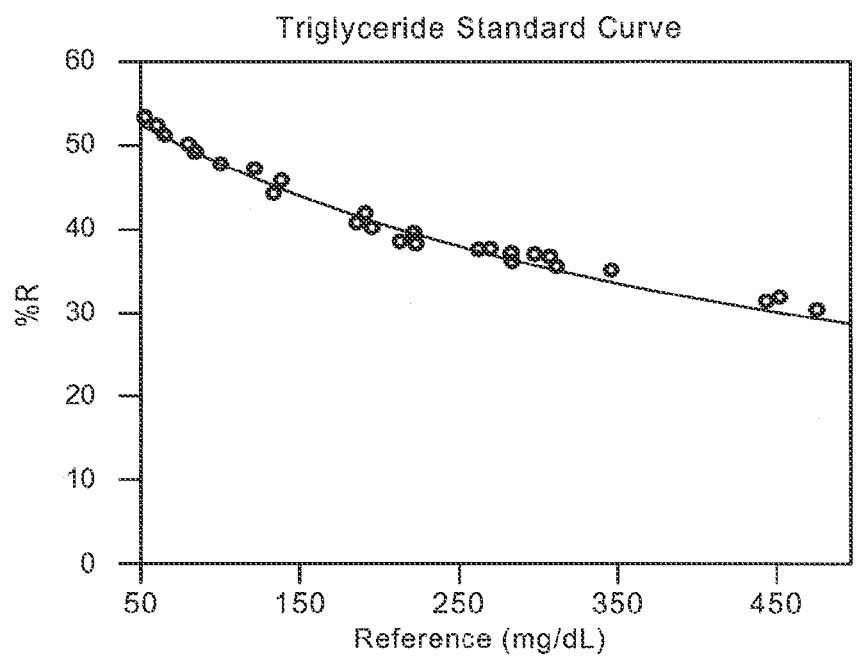
Figure 15:
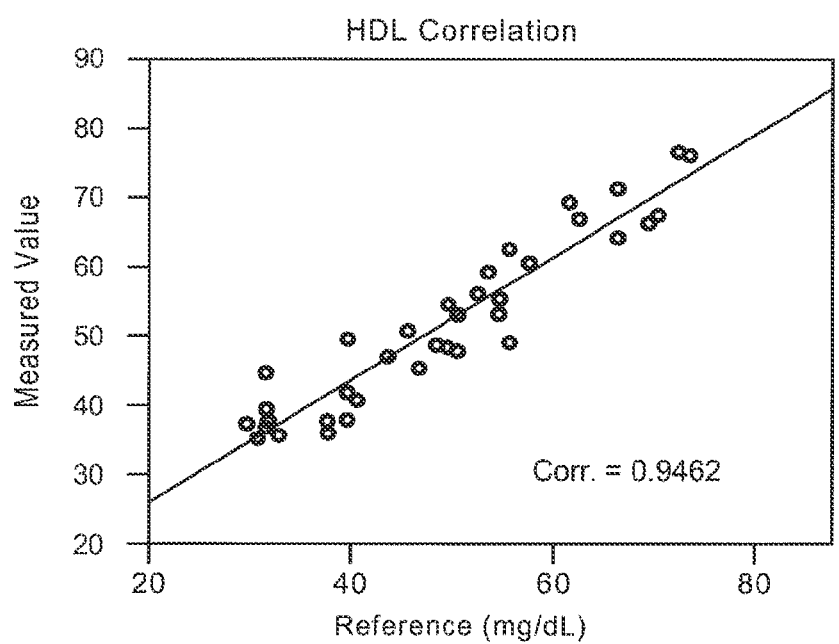
FIGS. 15-17 are graphs which plot measured value of concentration versus reference value for HDL, total cholesterol, and triglycerides, respectively.
Figure 16:
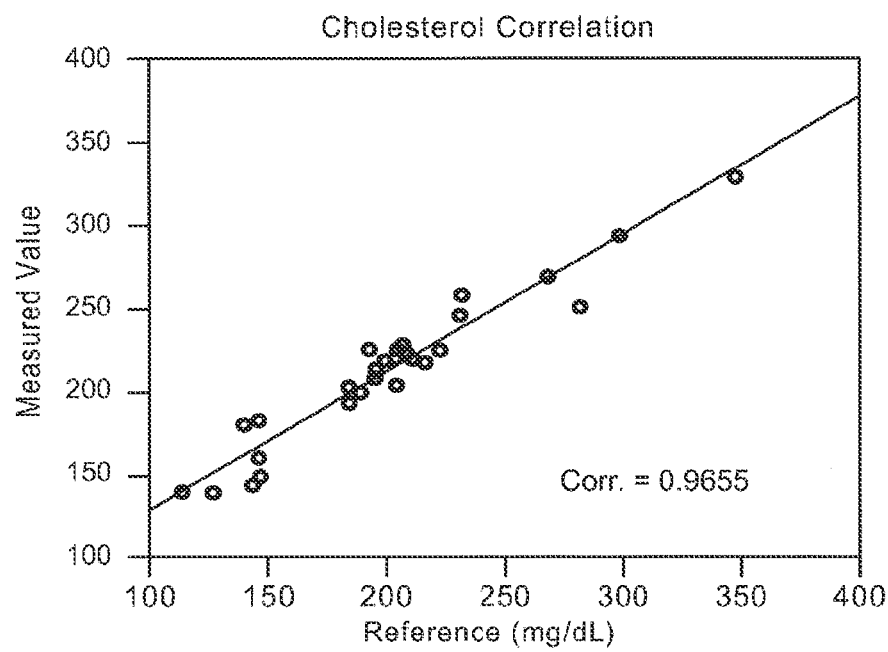

FIGS. 11-13 show calibration curves generated by plotting concentrations of blood samples against percent reflectance (% R) values read on a BioScanner Plus™ instrument. FIGS. 14-16 show plots of measured HDL, total cholesterol, and triglycerides, respectively, versus known concentration. As shown, the coefficient of correlation R2 in each case is very good.

The examples below illustrate construction of stacks for glucose and ketones, which could be substituted for or added to the matrix 36 described above.

Example 17

The following structure was constructed as per Example 15 for a multiple analytes hybrid test strip 20 that provides concentration of total cholesterol, HDL cholesterol, and glucose:
Disbursement layer 38 (Accuflow Plus P™)
Blood Separation Layer 40 (Ahlstrom Tuffglass™)
HDL fractionation layer 88
Untreated layers 94/100 (layers 88, 94, and 100 all made of CytoSep™ 1660)
Cholesterol Reaction Layers 90/96
Glucose Reaction Layer 102

Adhesive Layer 44

Solution for Impregnation of a Glucose Reaction Layer:
The following solution was used:

| | |
|---|---|
| Deionized water | 397.20 g |
| Glucose foundation | 537.30 g *See below |
| Gantrez (10%) | 19.40 g |
| Potassium ferricynide | 23.40 g |
| Adjust the pH to 4.7 with citric acid. | |
| MAOS | 4.67 g |
| Peroxidase | 700.90 ku |
| Glucose oxidase | 467.20 ku |
| 4-amino antipyrine | 4.21 g |

-continued

| | |
|---|---|
| Adjust the pH to 4.7-4.9. | |
| Adjust the volume to 1 liter with deionized water. | |
| Deionized water | 800.00 g |
| Triton x-100 | 1.86 g |
| Citric acid, monohydrate | 4.00 g |
| Sodium citrate, dehydrate | 54.00 g |
| Potassium EDTA | 1.30 g |
| PVP (40,000 daltons) | 60.00 g |
| Bovine serum albumin | 20.00 g |
| Adjust the pH to 4.7-4.9 | |
| Catalase | 50 U |
| Adjust the volume to 1 liter with deionized water. | |

*Glucose foundation

Example 18

Impregnation of Glucose Reaction Layer

The process is the same as that used for the cholesterol reaction layers 90 and 96 and triglycerides reaction layer 102. One suitable membrane for glucose reaction layer 102 is Thermopore™ from Pall Corporation.

Example 19

Calibration Curves

Calibration curves for the three chemistries (Total cholesterol, HDL cholesterol, and glucose) were generated as in Example 16. Several whole blood samples of known concentrations of HDL, total cholesterol, and glucose were tested by:
1. Applying a 35-40 microliter sample to opening 32 of hybrid test strip 20; and
2. Reading reflectance from the blue color on reaction layers (as seen through openings 34) on a portable whole blood analyzer (CardioChek PA™ instrument, Polymer Technology Systems).

Figure 17:
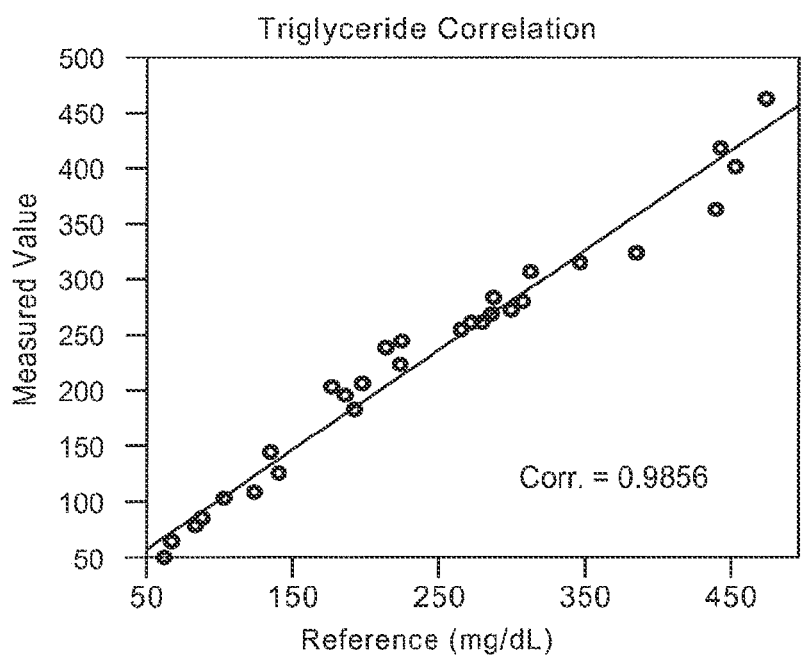
Figure 18:
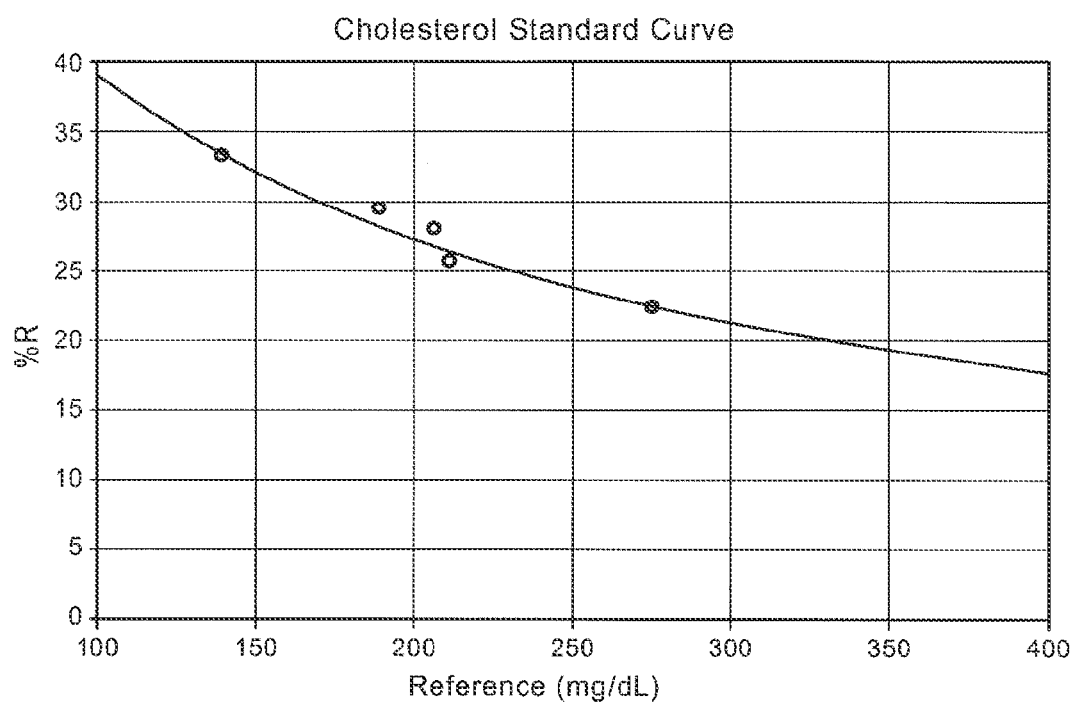
FIGS. 18-20 illustrate standard curves for cholesterol, HDL, and glucose, respectively.
Figure 19:
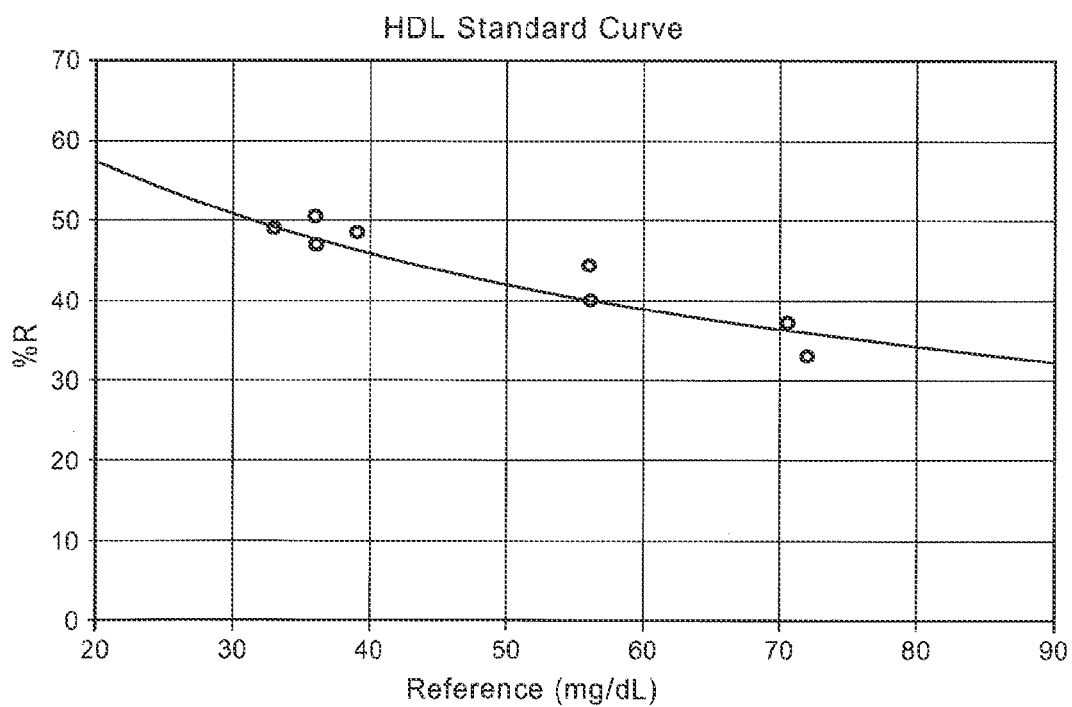
Figure 20:
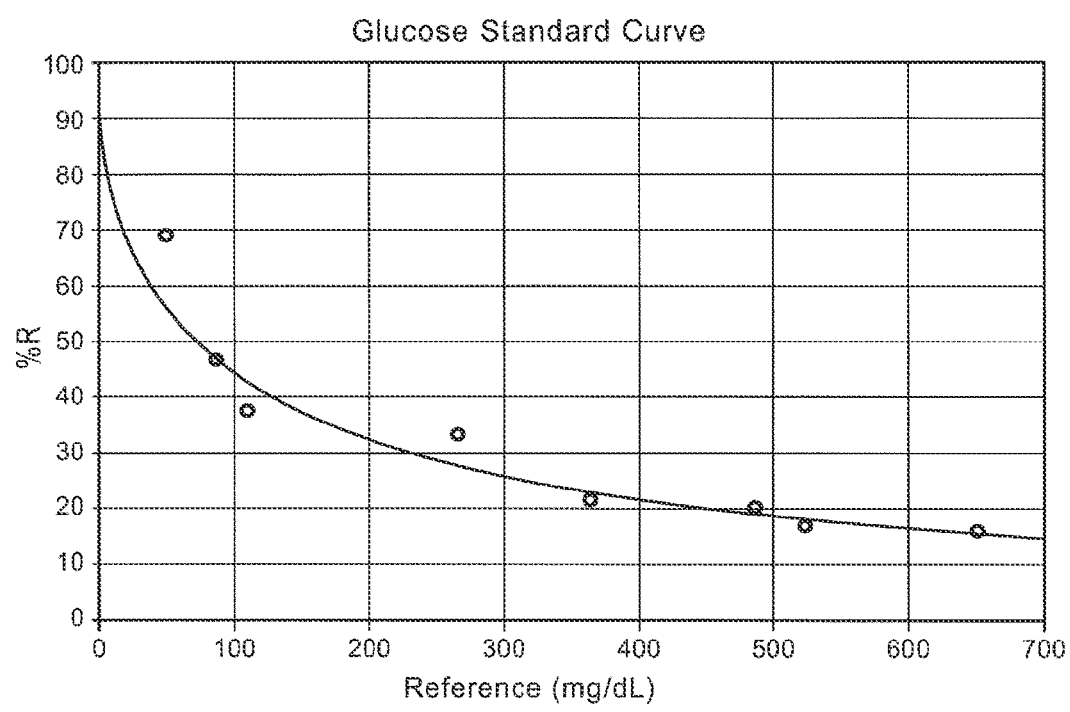

FIGS. 17-19 show calibration curves generated by plotting concentrations of blood samples against percent reflectance (% R) values read on a CardioChek PA™ instrument.

Example 20

Solution for Impregnation of a Ketone Reaction Layer

The following solution was used:

| | |
|---|---|
| Deionized water | 493.78 g |
| Igepal 660 | 0.99 g |
| Ketone foundation | 493.78 g *See below |
| Sodium chloride | 5.77 g |
| Oxamic acid, sodium salt | 0.55 g |
| Sucrose | 24.69 g |
| Adjust the pH to 7.9-8.1 | |
| NBT | 5.46 g |
| Diaphorase | 264.67 kU |
| Hydroxybutyrate dehydrogenase | 88.22 kU |
| Deionized water | 800.00 g |
| Sodium citrate, dehydrate | 24.00 g |
| Bovine serum albumin | 13.50 g |
| PVP (30,000 daltons) | 50.00 g |
| Adjust the pH to 7.9-8.1 | |
| Adjust the volume to 1 liter with deionized water. | |

*Ketone foundation

Example 21

Impregnation of Ketone Membrane

The process and membrane are the same as those used for glucose membrane 102 as described with reference to Example 18.

Test Method

A blood sample of approximately 30 to 50 microliters is contacted with the center of the top surface of elongated disbursement layer 38 of hybrid test strip 20. This is preferably performed by dispensing the sample from the tip of a micro pipette into application window 32. The blood sample then spreads substantially throughout the entire length of disbursement layer 32. As a second step, although not necessarily sequential from the spreading step, the blood sample is delivered uniformly from substantially the entire length of the bottom surface of disbursement layer 38 to blood separation layer 40, which is believed to retain about 80% to 90% of the red blood cells. The fluid having about 20% red blood cells remaining then is delivered to stacks 86, 92, and 98 (FIG. 5). As the sample moves vertically through these stacks, blank layers 88 and 100 retain any red blood cells that escape from layer 40, whereas layer 94 additionally precipitates and retains non-HDL cholesterol. Again, fluid moves through the stacks in a direction that is substantially normal to the plane defined by the stacks. While fluid movement is believed to be substantially completed within 10 to 20 seconds, it takes longer for color to develop in layers 90, 96, and 100. In about two (2) minutes, color development at the bottom of each stack has substantially reached an endpoint; and reflectance of each layer 90, 96, and 100 may be measured and correlated with cholesterol concentration as described above. Reflectance may be read and automatically converted to concentration by available optoelectronic instruments.

Since certain changes may be made in the above systems and methods without departing from the scope of the invention, it is intended that all subject matter contained in the above description or shown in the accompanying drawings may be interpreted as illustrative and not in a limiting sense.

We claim:

1. A method of determining concentrations of a plurality of analytes from a single blood sample, placed in a single opening, the method comprising:
   (a) placing said single blood sample in an opening;
   (b) absorbing said blood sample with a test matrix that includes a plurality of layers and a chromogenic agent, the test matrix including a disbursement layer;
   (c) generating a colored response with said test matrix wherein said colored response is proportional to a concentration of a first analyte;
   (d) drawing a portion of said single blood sample to a sample area by laterally spreading through the disbursement layer;
   (e) contacting said portion of said single blood sample with an electrode and a counter-electrode in the sample area; and
   (f) measuring an electrical property of said single blood sample though said electrode and counter-electrode wherein said electrical property is proportional to a concentration of a second analyte in said single blood sample.

2. A method of determining concentrations of a plurality of analytes from a single blood sample, the method comprising:
   (a) contacting said single blood sample with a top surface of an elongated disbursement layer and spreading said single blood sample substantially throughout an entire length of said disbursement layer;
   (b) contacting said single blood sample with a sample area such that a portion of said single blood sample is drawn to the sample area by passing through the disbursement layer;
   (c) delivering said single blood sample from said disbursement layer to a first stack, a second stack, and a third stack, each of said first, second, and third stacks positioned adjacent to and in constant contact with said disbursement layer,
   (d) moving the sample downward through the stacks in a direction substantially normal to the plane defined by the stacks;
   (e) producing a colored response at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample;
   (f) delivering the portion of the single blood sample drawn into the sample area to an electrode and a counter-electrode; and
   (g) measuring an electrical property of the single blood sample using the electrode and counter-electrode wherein the electrical property is proportional to the concentration of a fourth analyte in the blood sample.

3. A method as in claim 2 wherein at least one of said stacks includes a blank layer, said blank layer being a different layer than said disbursement layer, wherein said blank layer primarily functions to maintain all stacks at substantially the same thickness.

4. A method as in claim 2 wherein said first, second, and third analytes are Total Cholesterol, HDL Cholesterol, and Triglycerides, respectively.

5. A method as in claim 2 wherein said fourth analyte is glucose.

6. A method of determining concentrations of a plurality of analytes from a single blood sample, the method comprising:
   (a) contacting a single blood sample from a lance with a top surface of an elongated disbursement layer of a test strip and spreading said single blood sample substantially throughout an entire length of said disbursement layer;
   (b) contacting said single blood sample with a sample area of an electrochemical portion of the test strip, wherein a residual amount of said single blood sample remaining after the contacting of (a) is used;
   (c) delivering said single blood sample from said disbursement layer to a first stack, a second stack, and a third stack, each of said first, second, and third stacks positioned adjacent to and in constant contact with said disbursement layer,
   (d) moving the sample downward through the stacks in a direction substantially normal to the plane defined by the stacks;
   (e) producing a colored response at the bottom of each of the three stacks, the colored response at the bottom of the first stack being proportional to the concentration of a first analyte in the blood sample, the colored response at the bottom of the second stack being proportional to the concentration of a second analyte in the blood sample, and the colored response at the bottom of the third stack being proportional to the concentration of a third analyte in the blood sample; and (f) measuring an electrical property of the single blood sample using the electrode and counter-electrode in the electrochemical portion, wherein the electrical property is proportional to the concentration of a fourth analyte in the blood sample.

7. A method as in claim 6 wherein at least one of said stacks includes a blank layer, said blank layer being a different layer than said disbursement layer, wherein said blank layer primarily functions to maintain all stacks at substantially the same thickness.

8. A method as in claim 6 wherein said first, second, and third analytes are Total Cholesterol, HDL Cholesterol, and Triglycerides, respectively, and wherein said fourth analyte is glucose.

9. An apparatus for measuring concentration of multiple analytes in a whole blood sample, comprising:
(a) a test matrix comprising:
(i) an elongated porous disbursement layer;
(ii) a blood separation layer adjacent to the bottom surface of said disbursement layer; and
(iii) at least two vertically aligned stacks spaced apart and adjacent to the bottom surface of said blood separation layer wherein a first one of said vertically aligned stacks includes multiple layers, said multiple layers including a reagent and a chromagen;
(b) an electrochemical testing member comprising:
(i) a sample area;
(ii) an electrode; and
(iii) a counter-electrode wherein said electrode and counter-electrode are oriented in electrical communication with each other when a blood sample is present, and the electrode and the counter-electrode are located in the sample area; and
(c) a hybrid test strip holder having a top portion and a bottom portion sandwiching said test matrix therebetween; said top and bottom portions holding said electrochemical testing member; said top portion of said hybrid test strip holder having a sample application window exposing a top surface of said disbursement layer and a portion of the disbursement layer in contact with the sample area, such that blood from the disbursement layer may reach the sample area when a sample is present; and said bottom portion of said hybrid test strip holder having at least one test reading window through which bottom surfaces of said first and second stacks can be read.

10. An apparatus as in claim 9 wherein said sample application window is positioned within a periphery defined by said stacks.

11. An apparatus as in claim 9 wherein said bottom surfaces of said stacks are substantially coplanar.

12. An apparatus as in claim 9 wherein said blood separation layer comprises a glass fiber matrix.

13. An apparatus as in claim 9 wherein said electrochemical test panel further comprises:
(iv) enzymatic reactants overlaying said electrode and counter-electrode.

14. An apparatus as in claim 9 wherein a selectively permeable membrane is introduced between said electrode and counter-electrode in order to lessen interferents.

15. An apparatus as in claim 9 wherein a selective electrocatalyst is introduced in order to lessen interferents.

16. An apparatus as in claim 9 wherein said electrochemical testing member is interchangeable.

17. An apparatus for measuring concentration of multiple analytes in a whole blood sample, comprising:
(a) a test matrix comprising:
(i) an elongated porous disbursement layer;
(ii) a blood separation layer adjacent to the bottom surface of said disbursement layer; and
(iii) at least two vertically aligned stacks spaced apart and adjacent to the bottom surface of said blood separation layer wherein a first one of said vertically aligned stacks includes multiple layers, said multiple layers including a reagent and a chromagen;
(b) an electrochemical testing member comprising:
(i) a sample area;
(ii) an electrode; and
(iii) a counter-electrode wherein said electrode and counter-electrode are oriented in electrical communication with each other when a blood sample is present, and the electrode and the counter-electrode are located in the sample area; and
(c) a hybrid test strip holder having a top portion and a bottom portion sandwiching said test matrix there between; said top and bottom portions holding said electrochemical testing member; said top portion of said hybrid test strip holder having a sample application window exposing a top surface of said disbursement layer and the sample area, such that blood from a single sample in a lance is received in the sample area and said disbursement layer; and said bottom portion of said hybrid test strip holder having at least one test reading window through which bottom surfaces of said first and second stacks can be read.

18. An apparatus as in claim 17 wherein said sample application window is positioned within a periphery defined by said stacks.

19. An apparatus as in claim 17 wherein said bottom surfaces of said stacks are substantially coplanar.

20. An apparatus as in claim 17 wherein said blood separation layer comprises a glass fiber matrix.

* * * * *